United States Patent [19]
McGhee et al.

[11] Patent Number: 5,380,855
[45] Date of Patent: Jan. 10, 1995

[54] PROCESS FOR PREPARING N,N-SUBSTITUTED CARBAMOYL HALIDES

[75] Inventors: William D. McGhee, Bridgeton; John J. Talley, St. Louis, both of Mo.

[73] Assignee: Monsanto Company, St. Louis, Mo.

[21] Appl. No.: 192,322

[22] Filed: Feb. 4, 1994

[51] Int. Cl.$^6$ .................. C07B 41/08; C07D 211/06; C07C 269/06
[52] U.S. Cl. .................. 546/245; 562/844; 562/859; 562/862
[58] Field of Search ............... 546/245; 562/859, 862, 562/844

[56] References Cited

U.S. PATENT DOCUMENTS

| | | | |
|---|---|---|---|
| 4,467,089 | 8/1984 | Bechara | 544/351 |
| 4,542,214 | 9/1985 | Bechara | 544/107 |
| 5,055,577 | 10/1991 | Riley et al. | 544/172 |
| 5,189,205 | 2/1993 | McGhee et al. | 560/345 |
| 5,223,638 | 6/1993 | McGhee et al. | 560/24 |

OTHER PUBLICATIONS

Hoshino, et al., "A Convenient Preparation of Certain N,N-Dialkylcarbamoyl Chlorides", Synthetic Communications., 17(16), pp. 1887–1892 (1987).

Boger, et al., "Activation and Coupling of Pyrrole-1-carboxylic Acid in the Formation of Pyrrole N–Carbonyl Compounds: Pyrrole-1-carboxylic Acid Anhydride", J. Org. Chem., vol. 52, No. 11, 1987, pp. 2319–2323.

Bruneau et al., "Catalytic Synthesis of O-β-Oxoalkylcarbamates", Tetrahedron Letters, vol. 28, No. 18, pp. 2005–2008 (1987).

McGhee et al., "Palladium-Catalyzed Generation of O–Allylic Urethanes and Carbonates from Amines/Alcohols, Carbon Dioxide and Allylic Chlorides", Organometallics, vol. 12, No. 4, pp. 1429–1433 (1993).

Shim et al., "Synthesis of Carbamates from Amine, Acetylenic Alcohol, and CO$_2$ using Lanthanide as Catalysts", Bull. Korean Chem. Soc., vol. 11, No. 5, pp. 467–468, (1990).

Kirk–Othmer Encyclopedia of Chemical Technology, "Friedel–Crafts Reactions", vol. 11, Third Edition, p. 286, (1982).

Kirk–Othmer Encyclopedia of Chemical Technology, "Herbicides", vol. 12, Third Edition, pp. 324–325, (1982).

March, Advanced Organic Chemistry, Third Edition, pp. 388–389, (1985).

Primary Examiner—Johann Richter
Assistant Examiner—Michael B. Hydorn
Attorney, Agent, or Firm—Kenneth D. Goetz; Paul L. Passley; James C. Bolding

[57] ABSTRACT

A process for preparing N,N-substituted carbamoyl halides comprising (a) contacting carbon dioxide and a secondary amine in the presence of an aprotic organic solvent and a base selected from the group consisting of a phosphazene compound, an organic, nitrogenous base, mixtures of pyridine and a phosphazene compound or an organic, nitrogenous base, and mixtures thereof, to produce the corresponding ammonium carbamate salt, and (b) reacting the ammonium carbamate salt with a halide-containing electrophilic compound to produce the corresponding N,N-substituted carbamoyl halides. A second embodiment comprises recovering the ammonium carbamate salt of step (a) prior to reacting the ammonium carbamate salt with an halide-containing electrophilic compound in the presence of an aprotic organic solvent and a base selected from the group consisting of a phosphazene compound, an organic, nitrogenous base, mixtures of pyridine and a phosphazene compound or an organic, nitrogenous base, and mixtures thereof.

20 Claims, No Drawings

PROCESS FOR PREPARING N,N-SUBSTITUTED CARBAMOYL HALIDES

BACKGROUND OF THE INVENTION

The invention relates to a process for preparing N,N-substituted carbamoyl halides. In one aspect, the invention relates to a new and useful process for preparing N,N-substituted carbamoyl halides from secondary amines, carbon dioxide and a halide-containing electrophilic compound.

Carbamoyl halides, particularly carbamoyl chlorides, are useful intermediates in the preparation of unsymmetrical ureas and N,N-dialkyl carbamate esters. Carbamoyl chlorides are useful intermediates in the preparation of amides in direct Friedel-Crafts acylation of aromatics and the resulting amides can be hydrolyzed to the corresponding carboxylic acids. Carbamoyl chlorides are also useful intermediates in the preparation of thiocarbamate herbicides via the reaction of carbamoyl chlorides with a thiol (as the sodium alkylmercaptide).

Commercially, the phosgenation of ammonia and amines is by far the most widely used method for producing carbamoyl chlorides. For the preparation of N,N-substituted carbamoyl chlorides, the commercial process involves the phosgenation of secondary amine. The use of phosgene, however, has several disadvantages. The phosgenation route is long, energy intensive and requires handling highly corrosive materials, e.g. hydrogen chloride and chlorine, and highly toxic reagents and intermediates, e.g. phosgene and chlorine. Furthermore, the phosgenation route requires use of process equipment which can withstand high temperatures and highly corrosive conditions resulting in increased capital cost.

A non-phosgene process for preparing N,N-substituted carbamoyl halides which is economical, commercially viable and can produce N,N-substituted carbamoyl halides with good yields under extremely mild reaction conditions and short reaction times is highly desirable.

SUMMARY OF THE INVENTION

It is an object of the invention to provide a process for preparing N,N-substituted carbamoyl halides. It is a further object of the invention to provide an efficient and economic process for preparing N,N-substituted carbamoyl halides that is commercially viable. It is a still further object of the invention to provide a process for preparing N,N-substituted carbamoyl halides which can be utilized in the preparation of unsymmetrical ureas and N,N-dialkyl carbamate esters, aromatic amides, and thiocarbamate herbicides.

According to the invention, a process for preparing N,N-substituted carbamoyl halides is provided which comprises (a) contacting carbon dioxide and a secondary amine in the presence of an aprotic organic solvent and a base selected from the group consisting of a phosphazene compound, an organic, nitrogenous base, mixtures of pyridine and a phosphazene compound or an organic, nitrogenous base, and mixtures thereof, under conditions of time and temperature sufficient to produce the corresponding ammonium carbamate salt, and (b) reacting the ammonium carbamate salt with a halide-containing electrophilic compound under reaction conditions of time and temperature sufficient to produce the corresponding N,N-Substituted carbamoyl halide. In one embodiment, the ammonium carbamate salt of step (a) is recovered prior to reacting the ammonium carbamate salt with a halide-containing electrophilic compound in the presence of an aprotic organic solvent and a base selected from the group consisting of a phosphazene compound, an organic, nitrogenous base, mixtures of pyridine and a phosphazene compound or an organic, nitrogenous base, and mixtures thereof.

DETAILED DESCRIPTION OF THE INVENTION

A first embodiment of the invention relates to a process for preparing an N,N-substituted carbamoyl halide comprising (a) contacting $CO_2$ and a secondary amine in the presence of an aprotic organic solvent and a base selected from the group consisting of a phosphazene compound, an organic, nitrogenous base, mixtures of pyridine and a phosphazene compound or organic, nitrogenous base, and mixtures thereof, wherein the organic, nitrogenous base is selected from the group consisting of guanidine compounds, amidine compounds, tertiary amines, the secondary amine reactant, and mixtures thereof, under reaction conditions of time and temperature sufficient to produce the corresponding ammonium carbamate salt, and (b) reacting the ammonium carbamate salt with a halide-containing electrophilic compound under reaction conditions of time and temperature sufficient to produce the corresponding N,N-substituted carbamoyl halide, wherein halide is bromide or chloride.

A second embodiment of the invention relates to a process for preparing an N,N-substituted carbamoyl halide comprising (a) contacting $CO_2$ and a secondary amine in the presence of an aprotic organic solvent and a base selected from the group consisting of a phosphazene compound, an organic, nitrogenous base, mixtures of pyridine and a phosphazene compound or an organic, nitrogenous base, and mixtures thereof, wherein the organic, nitrogenous base is selected from the group consisting of guanidine compounds, amidine compounds, tertiary amines, the secondary amine reactant and mixtures thereof, under reaction conditions of time and temperature sufficient to produce the corresponding ammonium carbamate salt, (b) recovering the ammonium carbamate salt, and (c) reacting the ammonium carbamate salt with a halide-containing electrophilic compound in the presence of an aprotic organic solvent and a base selected from the group consisting of a phosphazene compound, an organic, nitrogenous base, mixtures of pyridine and a phosphazene compound or an organic, nitrogenous base, and mixtures thereof, under reaction conditions of time and temperature sufficient to produce the corresponding N,N-substituted carbamoyl halide, wherein halide is bromide or chloride.

The N,N-substituted carbamoyl halides made according to this invention are readily recoverable and well suited for use in preparation of unsymmetrical ureas, N,N-dialkyl carbamate esters, aromatic amides and thiocarbamate herbicides.

The N,N-substituted carbamoyl halides produced by the process of the invention can be represented by the formula:

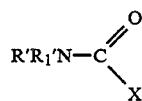

wherein R' and $R_1'$ are independently selected from the group consisting of alkyl, alkenyl, cycloalkyl, cycloalkenyl, aryl, aralkyl, aralkenyl, alkenaryl and alkaryl radicals, or wherein R' is a radical represented by the formula:

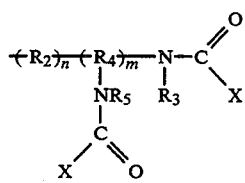

and $R_1'$ is as defined above, or wherein R' and $R_1'$ form a nitrogen-containing heterocycle, wherein $R_2$, $R_3$, $R_4$ and $R_5$ are independently selected from the group consisting of alkyl, alkenyl, cycloalkyl, cycloalkenyl, aryl, aralkyl, aralkenyl, alkenaryl and alkaryl radicals, m is a integer from 0 to 100, n is 0 or 1, and X is bromine or chlorine. In addition, R' and $R_1'$ may contain nonnucleophilic functional groups which do not react preferentially with the halide-containing electrophilic compound. Examples of suitable functional groups include esters, amides, urethanes, carbonates, and the like, and salts thereof.

As used herein, the term "alkyl", alone or in combination, means a straight-chain or branched-chain alkyl radical containing from 1 to about 22 carbon atoms, preferably 1 to about 18 carbon atoms. The term "alkenyl," alone or in combination, means an alkyl radical having one or more double bonds, and containing 2 to about 22 carbon atoms, preferably 2 to about 18 carbon atoms. The term "cycloalkyl", alone or in combination, means a cycloalkyl radical containing 3 to about 10, preferably 3 to about 8 carbon atoms. The term "cycloalkenyl", alone or in combination, means a cycloalkyl radical having one or more double bonds. The term "aryl", alone or in combination, means an aromatic radical containing 6 to about 18, preferably 6 to about 10 carbon atoms. The term "aralkyl", alone or in combination, means an alkyl or cycloalkyl radical as defined above in which one hydrogen atom is replaced by an aryl radical as defined above. The term "aralkenyl", alone or in combination, means an alkenyl or cycloalkenyl radical as defined above in which one hydrogen atom is replaced by an aryl radical as defined above. The term "alkaryl", alone or in combination means an aryl radical as defined above in which one hydrogen atom is replaced by an alkyl or cycloalkyl radical as defined above. The term "alkenaryl", alone or in combination, means an aryl radical as defined above in which one hydrogen atom is replaced by an alkenyl or cycloalkenyl radical as defined above. The term "nitrogen-containing heterocycle" means ring structures containing at least one nitrogen atom, in addition to carbon, in the ring. The total number of atoms in the heterocyclic ring structure is from 5 to about 10, preferably 5 to 6.

Examples of N,N-substituted carbamoyl halides produced by the process of the invention include, but are not limited to, N,N-dibutyl carbamoyl chloride, N,N-dibutyl carbamoyl bromide, piperidine carbamoyl chloride, piperidine carbamoyl bromide, N,N-dipropyl carbamoyl chloride, N,N-dipropyl carbamoyl bromide, N-phenyl, N-ethyl carbamoyl chloride, N-phenyl, N-ethyl carbamoyl bromide, and the like, and mixtures thereof.

The ammonium salt of the carbamate anion is prepared in solution in the presence of a base. The reaction between the secondary amine and carbon dioxide to form the ammonium carbamate salt may be represented by the equation (1). The resulting ammonium carbamate salt solutions are normally homogeneous.

$$RR_1NH + CO_2 + Base \rightleftharpoons RR_1NCO_2^- {}^+H\,Base \qquad (1)$$

The result of the reaction of the ammonium carbamate salt with the halide-containing electrophilic compound may be represented by the equation (2).

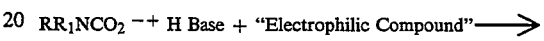

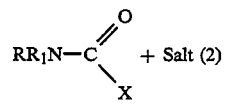

The secondary amines for use in the process of the invention are selected from the group consisting of compounds represented by the formula $RR_1NH$, wherein R and $R_1$ are independently selected from the group consisting of alkyl, alkenyl, cycloalkyl, cycloalkenyl, aryl, aralkyl, aralkenyl, alkenaryl and alkaryl radicals or wherein R is a radical represented by the formula:

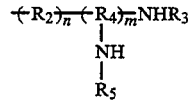

and $R_1$ is as defined above, or wherein R and $R_1$ form a nitrogen-containing heterocycle, wherein $R_2$, $R_3$, $R_4$, $R_5$, m and n are as defined above. Suitable secondary amines include di(secondary amines) and poly(secondary amines). In addition, R and $R_1$ may contain nonnucleophilic functional groups which do not react preferentially with the halide-containing electrophilic compound. Examples of suitable functional groups include esters, amides, urethanes, carbonates, and the like, and salts thereof.

Examples of secondary amines which can be employed in the process of the invention include dibutyl amine, piperidine, diethyl amine, dipropyl amine, ethyl butyl amine, diisopropyl amine, phenyl ethyl amine, and the like, and mixtures thereof.

Applicable solvents for use in the process of the invention are aprotic organic solvents. Both polar and non-polar aprotic organic solvents, as well as mixtures thereof, may be used in the process of the invention. As utilized herein, the phrase "polar aprotic organic solvent" means an aprotic organic solvent having a dielectric constant measured at 25° C. of greater than about 10 as reported in Reichardt, C., "Solvents and solvent effects in organic chemistry," 2nd ed., VCH Verlagsgesellschaft, Weinheim, (1988), Table A-1. Other methods for determining dielectric constants are known and suitable polar aprotic organic solvents are those having a dielectric constant greater than that of tetrahydrofuran utilizing any of such methods.

Examples of non-polar aprotic organic solvents which can be employed in the process of the invention include dichloromethane, toluene, tetrahydrofuran, o-dichlorobenzene, triethylamine and the like, and mixtures thereof. Currently preferred non-polar aprotic organic solvents include dichloromethane and toluene.

Examples of polar aprotic organic solvents which can be employed in the process of the invention include dimethyl formamide, N-methyl-2-pyrrolidone, N,N-dimethyl acetamide, dimethyl sulfoxide, acetonitrile, sulfolane, pyridine and the like, and mixtures thereof. Currently preferred polar aprotic organic solvents include acetonitrile and N,N-dimethyl acetamide.

Although not specifically required, it is preferred to utilize the same solvent to carry out both reaction steps of the present invention in order to avoid additional process equipment for recovering additional solvents.

The amount of solvent utilized in the process of the invention is preferably at least the amount necessary to solubilize the ammonium carbamate salt present.

The base utilized in the process of the invention is a phosphazene compound, an organic nitrogenous base, mixtures of pyridine and a phosphazene compound or an organic, nitrogenous base, or mixtures thereof. The phrase "organic, nitrogenous base" as used herein refers to a base other than the phosphazene compound or pyridine. Applicable organic, nitrogenous bases for use in the process of the invention include guanidine compounds, amidine compounds, tertiary amines, the secondary amine utilized as a reactant in the process of the invention, and mixtures of any two or more thereof. When the reactant secondary amine is used as the base, alone or in combination with another base, it is preferred to utilize an amount of secondary amine sufficient to serve as both the base and the reactant secondary amine.

The phosphazene compounds of the invention are compounds represented by the formula:

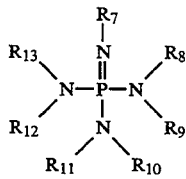

wherein $R_7$, $R_8$, $R_9$, $R_{10}$, $R_{11}$, $R_{12}$ and $R_{13}$ are independently selected from the group consisting of alkyl, aryl, alkaryl, aralkyl and cycloalkyl radicals; or one of $R_8$ or $R_9$ together with one of $R_{10}$ or $R_{11}$, one of $R_{12}$ or $R_{13}$ together with one of $R_{10}$ or $R_{11}$, and $R_7$ together with one of $R_8$ or $R_9$ or one of $R_{12}$ or $R_{13}$ independently form a nitrogen-containing heterocycle; or $R_8$ together with $R_9$, $R_{10}$ together with $R_{11}$, and $R_{12}$ together with $R_{13}$ independently represent a radical represented by the formula:

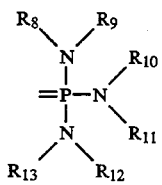

wherein $R_8$, $R_9$, $R_{10}$, $R_{11}$, $R_{12}$ and $R_{13}$ are as defined above.

Examples of phosphazene compounds which can be employed in the process of the invention include, but are not limited to, t-butyliminotris(dimethylamino)-phosphorane ($P_1$-tBu), 1-t-butyl-4,4,4-tris(dimethylamino)-2,2-bis-[tris (dimethylamino) phosphoranylideneamino]-2λ, 4λ-catenadi (phosphazene) ($P_4$-tBu), 2-t-butylimino-2-diethylamino-1,3-dimethyl-perhydro-1,3,2-diazaphosphorane (BEMP), t-butyliminotris (diethylamino) phosphorane, 2-t-octylimino-2-diethylamino-1,3-dimethyl-perhydro-1,3,2-diazaphosphorane, and the like, and mixtures of any two or more thereof.

The guanidine compounds of the invention are compounds represented by the formula:

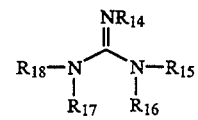

wherein $R_{14}$, $R_{15}$, $R_{16}$, $R_{17}$ and $R_{18}$ are independently selected from the group consisting of alkyl, aryl, alkaryl, aralkyl and cycloalkyl radicals; or $R_{14}$ together with one of $R_{15}$, $R_{16}$, $R_{17}$ or $R_{18}$, $R_{15}$ and $R_{16}$, and $R_{17}$ and $R_{18}$ independently form a nitrogen-containing heterocycle.

The amidine compounds of the invention are compounds represented by the formula:

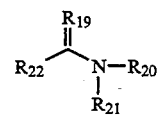

wherein $R_{19}$, $R_{20}$, $R_{21}$ and $R_{22}$ are independently selected from the group consisting of alkyl, aryl, alkaryl, aralkyl and cycloalkyl radicals; or $R_{19}$ together with $R_{20}$ or $R_{21}$ and $R_{22}$ together with $R_{20}$ or $R_{21}$ independently form a nitrogen-containing heterocycle.

Examples of organic, nitrogenous bases which can be employed in the process of the invention include triethylamine, diethyl isopropylamine, trimethylamine, piperidine, dibutylamine, diisopropylamine, phenyl ethylamine, ethyl butylamine, ethyl butylamine, tetramethyl guanidine (TMG), cyclohexyl-tetramethyl guanidine (CyTMG), butyltetraethyl guanidine (n-BTEG), cyclohexyl-tetraethyl guanidine (CyTEG), tetraethyl guanidine (TEG), t-butyl-tetraethyl guanidine (t-BTEG), 7-methyl-1,5,7-triazabicyclo[4.4.0]dec-5-ene (MTBD), t-butyl-dimethyl formamidine (t-BDMF), t-butyldimethyl acetamidine (t-BDMA), 1,5-diazabicyclo[4.3.0]non-5-ene (DBN), 1,8-diazabicyclo[5.4.0] undec-7-ene (DBU) and the like, and mixtures of any two or more thereof.

The amount of base, i.e., phosphazene compound, organic, nitrogenous base, mixtures of pyridine and a phosphazene compound or an organic, nitrogenous base, or mixture thereof, utilized in the process of the invention will depend upon the particular embodiment of the process.

In the first embodiment wherein the ammonium carbamate salt is not recovered prior to reaction with the halide-containing electrophilic compound, the amount of base can be conveniently expressed in terms of a ratio based on the number of equivalents of amine in the secondary amine charged. Broadly, the ratio of the number of moles of base to the number of equivalents of amine in the secondary amine will be about 1:1 to about the ratio of moles of the solvent to equivalents of amine in the secondary amine in the case where the base or a component of the base also serves as the solvent, preferably about 2:1 to about 10:1, and most preferably about 2:1 to about 4:1. The base can be completely charged at the beginning of the process, or a portion may be charged at the beginning of the process and the remainder charged at any time prior to the reaction of the ammonium carbamate salt with the halide-containing electrophilic compound. If the base used is the reactant secondary amine or a mixture containing the reactant secondary amine, the amount of secondary amine charged will be adjusted to account for the above base requirements.

In the second embodiment wherein the ammonium carbamate salt is recovered prior to reaction with the halide-containing electrophilic compound, the amount of base can be conveniently expressed in terms of a ratio based on the number of equivalents of amine in the secondary amine charged for the reaction of the secondary amine with carbon dioxide, and the amount of base can be conveniently expressed in terms of a ratio based on the number of equivalents of carbamate in the ammonium carbamate salt charged for the reaction of the ammonium carbamate salt with the halide-containing electrophilic compound. For the reaction of the secondary amine with carbon dioxide, the ratio of the number of moles of base to the number of equivalents of amine in the secondary amine will broadly be about 0.5:1 to about 10:1, preferably about 1:1 to about 4:1, and most preferably about 1:1 to about 2:1. If the base used is the reactant secondary amine or a mixture containing the reactant secondary amine, the amount of secondary amine charged will be adjusted to account for the above base requirements. For the reaction of the ammonium carbamate salt with the halide-containing electrophilic compound, the ratio of the number of moles of base to the number of equivalents of carbamate in the ammonium carbamate salt will broadly be about 0.5:1 to about 10:1, preferably about 1:1 to about 4:1, and most preferably about 1:1 to about 2:1.

Applicable halide-containing electrophilic compounds for use in the process of the invention include $POX_3$, $PX_3$, $PX_5$, $SOX_2$, $SO_2X_2$ and mixtures thereof where X is bromine or chlorine and halides are bromides and chlorides.

Examples of suitable halide-containing electrophilic compounds include $POCl_3$, $POBr_3$, $PCl_3$, $PBr_3$, $PCl_5$, $PBr_5$, $SOCl_2$, $SOBr_2$, $SO_2Cl_2$ and $SO_2Br_2$. The currently preferred halide-containing electrophilic compounds are the chloride-containing electrophilic compounds, specifically $POCl_3$ and $SOCl_2$ because of good results achievable with these compounds.

In the first embodiment wherein the ammonium carbamate salt is not recovered prior to reaction with the halide-containing electrophilic compound, the amount of halide-containing electrophilic compound can be conveniently expressed in terms of a ratio based on the number of equivalents of amine in the secondary amine reactant charged. If the base used is the reactant secondary amine or a mixture containing the reactant secondary amine, the amount of halide-containing electrophilic compound will be adjusted to account for the secondary amine which functions as the base. Broadly, the ratio of the number of moles of halide-containing electrophilic compound to the number of equivalents of amine in the secondary amine will be about 1:1 to about 10:1, preferably about 1:1 to about 4:1 and most preferably about 1:1 to about 1.5:1.

In the second embodiment wherein the ammonium carbamate salt is recovered prior to reaction with the halide-containing electrophilic compound, the amount of electrophilic compound can be conveniently expressed in terms of a ratio based on the number of equivalents of carbamate in the ammonium carbamate salt charged for the reaction of the ammonium carbamate salt with the halide-containing electrophilic compound. Broadly, the ratio of the number of moles of halide-containing electrophilic compound to the number of equivalents of carbamate in the ammonium carbamate salt will be about 1:1 to about 10:1, preferably about 1:1 to about 4:1, and most preferably about 1:1 to about 1.5:1.

The reaction between the secondary amine and carbon dioxide is conducted under a $CO_2$ atmosphere. The pressure of $CO_2$ during this reaction is 0 psig (atmospheric pressure) to about 150 psig, preferably 0 psig to about 100 psig, and most preferably 0 psig to about 80 psig. It is preferred to charge the $CO_2$ to the reaction vessel containing the secondary amine below the liquid level in the reaction vessel. Although not specifically required, it is preferred to conduct the reaction of ammonium carbamate salt with halide-containing electrophilic compound under a $CO_2$ atmosphere. However, the reaction of ammonium carbamate salt with halide-containing electrophilic compound can be conducted under any inert atmosphere, e.g. nitrogen, argon or air, provided the atmosphere is substantially dry. A substantially dry atmosphere is desired because water will react with the halide-containing electrophilic compound. The pressure during this reaction is 0 psig to about 150 psig, preferably 0 psig to about 100 psig, and most preferably 0 psig to about 80 psig.

The temperature and time used in the process of the invention will depend on the particular reaction involved. For the reaction of secondary amine with $CO_2$, the temperature is about $-78°$ C. to about 50° C., preferably about $-20°$ C. to about 30° C., and most preferably about 20° C. to about 30° C. The time will broadly be the time required to achieve complete mixing of reactants to about 6 hours, preferably about 5 minutes to about 2 hours, and most preferably about 15 minutes to about 60 minutes. For the reaction of ammonium carbamate salt with halide-containing electrophilic compound, the temperature is about $-78°$ C. to about 25° C., preferably about $-40°$ C. to 10° C., and most preferably about $-20°$ C. to about 0° C. The time will broadly be the time required to achieve complete mixing of the reactants to about 4 hours, preferably about 1 minute to about 2 hours, and most preferably about 5 minutes to about 60 minutes.

For the embodiment where the ammonium carbamate salt is recovered prior to reaction with the halide-containing electrophilic compound, the ammonium carbamate salt can be recovered by any conventional means known in the art.

The desired N,N-substituted carbamoyl halides produced by the process of the invention can be recovered by any conventional means known in the art, such as that disclosed in the examples herein.

Contemplated equivalence of the general formulas set forth above for the secondary amines, N,N-substituted carbamoyl halides and halide-containing electrophilic compounds are compounds otherwise corresponding thereto and having the same general properties, such as wherein one or more of the various R groups are simple variations of the substituents as defined therein.

In addition, where a substituent is designated as, or can be, a hydrogen, the exact chemical nature of a substituent which is other than hydrogen at that position is not critical so long as it does not adversely effect the overall synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The invention will now be further disclosed in the following illustrative examples wherein parts and percentages are given on a molar basis unless otherwise specified.

EXAMPLES

All amines used in the following examples were obtained either from Aldrich Chemical Company or Kodak Chemical Company and were used as received. Toluene, methylene chloride and triethylamine were purchased from Aldrich Chemical Company. Pyridine was obtained from Fisher Scientific, $POCl_3$ was obtained from Aldrich Chemical and $SOCl_2$ was obtained from Kodak Chemical Company. CyTEG (N-cyclohexyl-N',N',N'',N''-tetraethyl guanidine) and CyTMG (N-cyclohexyl-N', N', N'', N''-tetraethyl guanidine) were synthesized according to the general procedure set forth in Bredereck, H. and Bredereck, K., Chem. Ber., 94, 2278–2295 (1961). DBU (1,8-diazabicyclo [5.4.0] undec-7-ene) was obtained from Aldrich Chemical Co. and MTBD (7-methyl-1,5,7-triazabicyclo [4.4.0] dec-5-ene) was obtained from Fluka Chemical Corp. Carbon dioxide was supplied either from Matheson (bone dry grade) or from Acetylene Gas Company (welding grade) and used without any further purification.

Gas chromatographic analysis was performed on a Varian model 3400 gas chromatograph with a model 8000 auto sampler using a 30 meter Megabore DB-1 (3 μm) J&W Scientific column.

EXAMPLE 1

Piperidine Carbamoyl Chloride: In a 100 mL round bottom flask was added 0.02 mol piperidine, 0.02 mol pyridine, 0.02 mol CyTMG, 1 mmol biphenyl as G.C. internal standard and 20 mL toluene. This solution was cooled to −10° C. using an ice salt bath and carbon dioxide was added subsurface to the cooled solution for 30 min. After this period of time the preformed carbamate solution was added all at once by cannula to a cooled (−10° C.) toluene (20 mL) solution of thionyl chloride (0.02 mol). The reaction mixture was stirred at −10° C. for 15 min. under atmospheric $CO_2$ pressure.

An aliquot was taken, diluted with diethyl ether, extracted with 0.5M aqueous HCl and analyzed by G.C. G.C. yield of piperidine carbamoyl chloride was determined to be 79% (Run 1).

Additional runs (Runs 2–14) were made according to the above procedure varying the type of base, solvent and halide-containing electrophilic compound. The results of all runs can be found in Table I.

EXAMPLE 2

N,N-Dibutyl Carbamoyl Chloride: In a 100 mL round bottom flask was added 6.45 g (0.05 mol) dibutyl amine, 4 g (0.05 mol) pyridine, 12.7 g (0.05 mol) N-cyclohexyl-N', N', N'', N''-tetraethylguanidine and 40 mL toluene. This solution was cooled to −10° C. using an ice salt bath and carbon dioxide was added subsurface to this cooled solution for 30 min. After this period of time the preformed carbamate solution was added all at once by cannula to a cooled (−10° C.) toluene (40 mL) solution of thionyl chloride (6 g, 0.05 mol). The reaction mixture was allowed to stir at −10° C. for 45 min.

The crude reaction mixture was poured into 100 mL 0.1M aqueous HCl giving rise to two layers. The organic layer was separated, dried over anhydrous $MgSO_4$, filtered and the solvent removed in vacuo. The residue was distilled under vacuum at 95°–98° C. giving 7.62 g (79% yield) of N,N-dibutyl carbamoyl chloride. I.R. (film) 1734.

EXAMPLE 3

Piperidine Carbamoyl Chloride: In a 100 mL round bottom flask was added 4.25 g (0.05 mol) piperidine, 4 g (0.05 mol) pyridine, 12.7 g (0.05 mol) N-cyclohexyl-N', N', N'', N''-tetraethylguanidine and 40 mL toluene This solution was cooled to −100° C. using an ice salt bath and carbon dioxide was added subsurface to this cooled solution for 30 min. After this period of time the preformed carbamate solution was added all at once by cannula to a cooled (−10° C.) toluene (40 mL) solution of thionyl chloride (6 g, 0.05 mol). The reaction mixture was allowed to stir at −10° C. for 30 min.

The crude reaction mixture was poured into 100 mL 0.1M aqueous HCl giving rise to two layers. The organic layer was separated, dried over anhydrous $MgSO_4$, filtered and the solvent removed in vacuo. The residue was distilled under vacuum at 82°–84° C. giving 4.22 g (52% yield) of piperidine carbamoyl chloride. I.R. (film) 1732.

TABLE I

| Run No. | Base[2] | Electrophilic Compound | Solvent | % Yield[1] Carbamoyl Chloride |
|---|---|---|---|---|
| 1 | CyTMG/pyr | $SOCl_2$ | Toluene | 79 |
| 2 | CyTEG | $POCl_3$ | $CH_2Cl_2$ | 67 |
| 3 | CyTEG | $POCl_3$ | Toluene | 67 |
| 4 | CyTEG | $SOCl_2$ | $CH_2Cl_2$ | 44 |
| 5 | CyTEG | $SOCl_2$ | Toluene | 72 |
| 6 | CyTEG/pyr | $SOCl_2$ | Toluene | 85 |
| 7 | CyTEG/2pyr | $SOCl_2$ | Toluene | 87 |
| 8 | CyTEG/pyr | $SOCl_2$ | $CH_2Cl_2$ | 80 |
| 9 | DBU/pyr | $SOCl_2$ | Toluene | 89 |
| 10 | MTBD/pyr | $SOCl_2$ | Toluene | 93 |
| 11 | (i-Pr)$_2$NEt/pyr | $SOCl_2$ | Toluene | 82 |
| 12 | $Et_3N$/pyr | $SOCl_2$ | Toluene | 45 |
| 13 | Piperidine/pyr | $SOCl_2$ | Toluene | 77 |

TABLE I-continued

| Run No. | Base[2] | Electrophilic Compound | Solvent | % Yield[1] Carbamoyl Chloride |
|---|---|---|---|---|
| 14 | Piperidine/pyr | SOCl$_2$ | CH$_2$Cl$_2$ | 75 |

[1]All yields were determined by gas chromatographic analysis using biphenyl as an internal standard.
[2]pyr = pyridine, Et$_3$N = triethylamine, (i-Pr)$_2$NEt = diisopropyl ethylamine.

That which is claimed is:

1. A process for preparing an N,N-substituted carbamoyl halide comprising:
   (a) contacting CO$_2$ and a secondary amine in the presence of an aprotic organic solvent and a base selected from the group consisting of a phosphazene compound, an organic nitrogenous base, and a mixture of pyridine and a phosphazene compound or an organic nitrogenous base, or mixtures thereof, wherein said organic nitrogenous base is selected from the group consisting of guanidine compounds, amidine compounds, tertiary amines, and said secondary amine, or mixtures thereof, under reaction conditions of time and temperature sufficient to produce the corresponding ammonium carbamate salt, and
   (b) reacting said ammonium carbamate salt with a halide containing electrophilic compound selected from the group consisting of POX$_3$, PX$_3$, PX$_5$, SOX$_2$, and SO$_2$X$_2$, or mixtures thereof, wherein X is bromine or chlorine and halide is bromide or chloride, under reaction conditions of time and temperature sufficient to produce the corresponding N,N-substituted carbamoyl halide.

2. The process according to claim 1 wherein said secondary amine is represented by the formula RR$_1$NH wherein R and R$_1$ are independently selected from the group consisting of alkyl, alkenyl, cycloalkyl, cycloalkenyl, aryl, aralkyl, aralkenyl, alkaryl and alkenaryl radicals, or wherein R is a radical represented by the formula

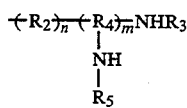

and R$_1$ is as defined above, or wherein R and R$_1$ form a nitrogen-containing heterocycle, or R and R$_1$ as defined above containing nonnucleophilic functional groups; wherein R$_2$, R$_3$, R$_4$, and R$_5$ are independently selected from the group consisting of alkyl, alkenyl, cycloalkyl, cycloalkenyl, aryl, aralkyl, aralkenyl, alkaryl and alkenaryl radicals, m is an integer from 0 to 100, and n is 0 or 1.

3. The process according to claim 2 wherein said nonnucleophilic functional groups are selected from the group consisting of esters, amides, urethanes, and carbonates, or salts thereof.

4. The process of claim 2 wherein said N,N-substituted carbamoyl halide is represented by the formula

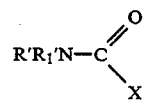

wherein R' and R$_1$' are independently selected from the group consisting of alkyl, alkenyl, cycloalkyl, cycloalkenyl, aryl, aralkyl, aralkenyl, alkaryl and alkenaryl radicals, or wherein R' is a radical represented by the formula

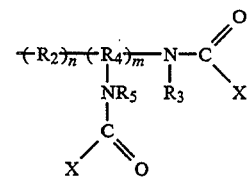

and R$_1$' is as defined above, or wherein R' and R$_1$' form a nitrogen-containing heterocycle, or R' and R$_1$' as defined above containing nonnucleophilic functional groups; wherein R$_2$, R$_3$, R$_4$ and R$_5$ are independently selected from the group consisting of alkyl, alkenyl, cycloalkyl, cycloalkenyl, aryl, aralkyl, aralkenyl, alkaryl and alkenaryl radicals, m is an integer from 0 to 100, and n is 0 or 1.

5. The process according to claim 4 wherein said nonnucleophilic functional groups are selected from the group consisting of esters, amides, urethanes, and carbonates, or salts thereof.

6. The process according to claim 1 wherein said base is a mixture of pyridine and a phosphazene compound or an organic nitrogenous base, and said halide-containing electrophilic compound is SOX$_2$ or SO$_2$X$_2$.

7. The process according to claim 1 wherein said base is said secondary amine or a mixture of pyridine and said secondary amine.

8. The process according to claim 1 wherein said aprotic organic solvent is a nonpolar aprotic organic solvent.

9. The process according to claim 1 wherein the ratio of the number of moles of said halide-containing electrophilic compound to the number of equivalents of amine in said secondary amine starting material is about 1:1 to about 10:1.

10. The process according to claim 1 wherein X is chlorine and said N,N-substituted carbamoyl halide is N,N-substituted carbamoyl chloride.

11. A process for preparing N,N-substituted carbamoyl halide comprising:
   (a) contacting CO$_2$ and a secondary amine in the presence of an aprotic organic solvent and a base selected from the group consisting of phosphazene compound, an organic nitrogenous base, and a mixture of pyridine and a phosphazene compound or an organic nitrogenous base, or mixtures thereof, wherein said organic nitrogenous base is selected from the group consisting of guanidine compounds, amidine compounds, tertiary amines, and said secondary amine, or mixtures thereof, under reaction conditions of time and temperature sufficient to produce the corresponding ammonium carbamate salt,
   (b) recovering said ammonium carbamate salt, and
   (c) reacting said ammonium carbamate salt with a halide-containing electrophilic compound selected from the group consisting of POX$_3$, PX$_3$, PX$_5$, SOX$_2$, and SO$_2$X$_2$, or mixtures thereof, wherein X is bromine or chlorine and halide is bromide or chloride, in the presence of an aprotic organic solvent and a base selected from the group consisting of a phosphazene compound, an organic, nitrogenous base, and a mixture of pyridine and a phosphazene compound or an organic nitrogenous base, and mixtures thereof, under reaction conditions of time and temperature sufficient to produce the corresponding N,N-substituted carbamoyl halide.

12. The process according to claim 11 wherein said secondary amine is represented by the formula $RR_1NH$ wherein R and $R_1$ are independently selected from the group consisting of alkyl, alkenyl, cycloalkyl, cycloalkenyl, aryl, aralkyl, aralkenyl, alkaryl and alkenaryl radicals, or wherein R is a radical represented by the formula

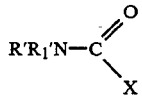

and $R_1$ is as defined above, or wherein R and $R_1$ form a nitrogen-containing heterocycle, or R and $R_1$ as defined above containing nonnucleophilic functional groups; wherein $R_2$, $R_3$, $R_4$, and $R_5$ are independently selected from the group consisting of alkyl, alkenyl, cycloalkyl, cycloalkenyl, aryl, aralkyl, aralkenyl, alkaryl and alkenaryl radicals, m is an integer from 0 to 100, and n is 0 or 1.

13. The process according to claim 12 wherein said nonnucleophilic functional groups are selected from the group consisting of esters, amides, urethanes, and carbonates, or salts thereof.

14. The process of claim 12 wherein said carbamoyl halide is represented by the formula

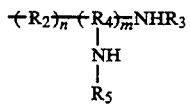

wherein R' and $R_1'$ are independently selected from the group consisting of alkyl, alkenyl, cycloalkyl, cycloalkenyl, aryl, aralkyl, aralkenyl, alkaryl and alkenaryl radicals, or wherein R' is a radical represented by the formula

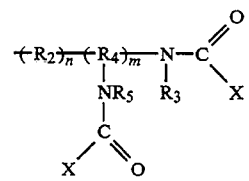

and $R_1'$ is as defined above, or wherein R' and $R_1'$ form a nitrogen-containing heterocycle, or R' and $R_1'$ as defined above containing nonnucleophilic functional groups; wherein $R_2$, $R_3$, $R_4$ and $R_5$ are independently selected from the group consisting of alkyl, alkenyl, cycloalkyl, cycloalkenyl, aryl, aralkyl, aralkenyl, alkaryl and alkenaryl radicals, m is an integer from 0 to 100, and n is 0 or 1.

15. The process according to claim 14 wherein said nonnucleophilic functional groups are selected from the group consisting of esters, amides, urethanes, and carbonates, or salts thereof.

16. The process according to claim 11 wherein said base is a mixture of pyridine and a phosphazene compound or an organic nitrogenous base, and said halide-containing electrophilic compound is $SOX_2$ or $SO_2X_2$.

17. The process according to claim 11 wherein said base is said secondary amine or a mixture of pyridine and said secondary amine.

18. The process according to claim 11 wherein said aprotic organic solvent is a nonpolar aprotic organic solvent.

19. The process according to claim 11 wherein the ratio of the number of moles of said halide-containing electrophilic compound to the number of equivalents of amine in said secondary amine starting material is about 1:1 to about 10:1.

20. The process according to claim 11 wherein X is chlorine and said N,N-substituted carbamoyl halide is N,N-substituted carbamoyl chloride.

* * * * *